(12) United States Patent
Huang (10) Patent No.: US 11,844,389 B2
(45) Date of Patent: Dec. 19, 2023

(54) HEAD-MOUNTED WELDING MASK

(71) Applicant: WUHAN WELHEL PHOTOELECTRIC CO., LTD, Wuhan (CN)

(72) Inventor: Shangyou Huang, Wuhan (CN)

(73) Assignee: Wuhan Welhel Photoelectric Co., Ltd, Wuhan (CN)

( * ) Notice: Subject to any disclaimer, the term of this patent is extended or adjusted under 35 U.S.C. 154(b) by 275 days.

(21) Appl. No.: 17/417,013

(22) PCT Filed: Nov. 25, 2019

(86) PCT No.: PCT/CN2019/120757
§ 371 (c)(1),
(2) Date: Jun. 21, 2021

(87) PCT Pub. No.: WO2020/134796
PCT Pub. Date: Jul. 2, 2020

(65) Prior Publication Data
US 2022/0071334 A1     Mar. 10, 2022

(30) Foreign Application Priority Data

Dec. 25, 2018 (CN) .......................... 201822188603.5

(51) Int. Cl.
  *A42B 3/22* (2006.01)
  *A61F 9/06* (2006.01)
(52) U.S. Cl.
  CPC ................ *A42B 3/222* (2013.01); *A61F 9/06* (2013.01)
(58) Field of Classification Search
  CPC . A61F 9/06; A61F 9/067; A61F 9/061; A42B 3/18; A42B 3/22; A42B 3/221;
  (Continued)

(56) References Cited

U.S. PATENT DOCUMENTS

| 8,434,168 B2 | 5/2013 | Paulson |
| 2012/0084904 A1 | 4/2012 | Paulson |
| 2016/0183622 A1* | 6/2016 | Patel ...................... A42B 3/222 |
| | | 2/424 |

FOREIGN PATENT DOCUMENTS

| CN | 87214607 U | 7/1988 |
| CN | 2507431 Y | 8/2002 |
(Continued)

OTHER PUBLICATIONS

English Translation of International Search Report for International application No. PCT/CN2019/120757; dated Feb. 28, 2020.
(Continued)

*Primary Examiner* — Khoa D Huynh
*Assistant Examiner* — Erick I Lopez
(74) *Attorney, Agent, or Firm* — Hoffman Warnick LLC; Franklin S. Abrams (57) ABSTRACT

The present disclosure provides a head-mounted welding mask, which includes a mask shell, a head-mounted mechanism, and a flip device, the flip device includes a knob which is connected to the mask shell, a link mechanism which is connected to the knob, and a base which is connected to the head-mounted mechanism, the link mechanism is disposed on the base, when the knob is moved, the knob drives the link mechanism to reciprocate in an arc, so that the mask shell flips relative to the head-mounted mechanism, and the barycenter of the mask shell moves into a predetermined range that is determined based on the gravity line where the barycenter of the head-mounted mechanism is located. The flip device changes the position of the barycenter of the mask shell through the movement of the link mechanism, so that the barycenter of the mask shell moves into a predetermined range that is determined based on the gravity line where the barycenter of the head-mounted mechanism is
(Continued)

located. And reduces the pressure on welder's head after the mask shell is flipped up.

8 Claims, 6 Drawing Sheets

(58) Field of Classification Search
CPC ......... A42B 3/222; A42B 3/223; A42B 3/225; A42B 3/226
See application file for complete search history.

(56) References Cited

FOREIGN PATENT DOCUMENTS

| CN | 2896942 Y | 5/2007 |
|---|---|---|
| CN | 108938192 A | 12/2018 |
| CN | 109498270 A | 3/2019 |
| CN | 209474952 U | 10/2019 |

OTHER PUBLICATIONS

English Translation of Written Opinion for International application No. PCT/CN2019/120757 ; dated Feb. 28, 2020.
International Search Report for International application No. PCT/CN2019/120757 ; dated Feb. 28, 2020.
Written Opinion for International application No. PCT/CN2019/120757 ; dated Feb. 28, 2020.
English translation of relevant portions of CN2896942Y; published May 9, 2007.
English translation of relevant portions of CN108938192A; published Dec. 7, 2018.
English translation of relevant portions of CN87214607U; published Jul. 6, 1988.

* cited by examiner

HEAD-MOUNTED WELDING MASK

CROSS-REFERENCE TO RELATED APPLICATIONS

This application is a national phase filing under 35 U.S.C. § 371 of PCT International Application PCT/CN2019/120757, filed Nov. 25, 2019, and published under PCT Article 21(2) in Chinese as WO/2020/134796 on Jul. 2, 2020. PCT/CN2019/120757 claimed priority benefit of China Patent Application No. 201822188603.5 filed Dec. 25, 2018. The above identified applications are hereby incorporated by reference in their entirety.

FIELD OF THE INVENTION

The present disclosure relates to the field of welding protection, and more particularly relates to a head-mounted welding mask.

BACKGROUND OF THE INVENTION

Welding arc always occurs during a metal welding process. The welding arc is a phenomenon of gas discharge between electrode and welding material, which contains a considerable amount of intense visible light, infrared rays, and ultraviolet rays. Optical radiation from the intense visible light, infrared rays and ultraviolet rays cause impairment to the eyes of a welder.

A welding helmet is used to shield a welder from occupational hazards in welding. It may not only protect the eyes of the welder, but also facilitate accurate positioning and efficient welding during a welding process. A head-mounted welding mask usually comprises a mask shell and a headband disposed on the mask shell and worn by a welder. During welding, the welder needs to turn the mask shell to check the welding status.

In prior art, when flip up the mask shell, the mask shell rotating around an axis which is located on the headband, so as to realize rotation function. Since the position of barycenter of the mask shell is usually below the axis, and there is a certain distance from the barycenter to the center of axis, when flip up, the path of the barycenter is a circle, take the axis as the center of the circle and the distance between the barycenter and the axis as the radius. After being flipped up, the barycenter of the mask shell locates former, generally locates on the former position of the barycenter of the headband, forms a forward flip torque between the two barycenters, may be make heavier oppressive feeling to welder's forehead. Another drawback is that, after being flipped up, the barycenter of the mask shell is far away from welder's head, further increased the oppressive. Therefore, the comfort of wearing the welding mask is very poor, which affects the work efficiency.

Therefore, it is necessary to provide a new head-mounted welding mask to eliminate the above drawback.

SPECIFIC DESCRIPTION

An object of the present disclosure is to provide a head-mounted welding mask, to solve the problem existing in conventional head-mounted welding mask, such as after been flipped up, the barycenter of the mask shell moves former, make heavier oppressive feeling to the welder's forehead, results in the poor wearing experience.

In order to achieve the above purpose, the disclosure provides the following technical solutions: A head-mounted welding mask, which includes a mask shell 1, a head-mounted mechanism 2, and a flip device 3 configure to connect the mask shell 1 and the head-mounted mechanism 2, the flip device 3 includes a knob 31 which is connected to the mask shell 1, a link mechanism 32 which is connected to the knob 31, and a base 33 which is connected to the head-mounted mechanism 2, the link mechanism 32 is disposed on the base 33, when the knob 31 is moved, the knob 31 drives the link mechanism 32 to reciprocate in an arc, so that the mask shell 1 flips relative to the head-mounted mechanism 2, and the barycenter of the mask shell 1 moves into a predetermined range that is determined based on the gravity line where the barycenter of the head-mounted mechanism 2 is located.

In one embodiment of the present disclosure, the link mechanism 32 includes at least a first link lever 321, a second link lever 322, and a third link lever 323, the first link lever 321 is connected to the knob 31 fixedly, the second link lever 322 is rotatable connected to the first link lever 321 and the base 33 respectively, and the third link lever 323 is rotatable connected to the first link lever 321 and the base 33, respectively.

In another embodiment of the present disclosure, the first link lever 321 includes two first-link-lever-movable-ends 3211, and the second link lever 322 includes a second-link-lever-movable-end 3221 and a second-link-lever-base-end 3222, The third link lever 323 includes a third-link-lever-movable-end 3231 and a third-link-lever-base-end 3232, the base 33 includes two base-fixed-ends 331, and the two first-link-lever-movable-ends 3211 are respectively rotatable connected to the second-link-lever-movable-end 3221 and the third-link-lever-movable-end 3231, and the two base-fixed-ends 331 are respectively rotatable connected to the second-link-lever-base-end 3222 and the third-link-lever-base-end 3232.

In one embodiment of the present disclosure, the second link lever 322 provides a first notch 3225, and the third-link-lever-movable-end 3231 is disposed in the first notch 3225.

In one embodiment of the present disclosure, the second link lever 322 provides a first limit block 3226, configure to positioning the first link lever 321.

In one embodiment of the present disclosure, the base 33 provides a second limit block 332, configure to positioning the third-link-lever-movable-end 3231.

In one embodiment of the present disclosure, the base 33 provides a third limit block 333, configure to positioning the third-link-lever-base-end 3232.

In one embodiment of the present disclosure, the head-mounted mechanism 2 is a headband or a safety helmet.

In one embodiment of the present disclosure, the head-mounted welding mask further includes an angle adjustment device 4, configure to adjust the angle between the mask shell 1 and the welder's eyes, the angle adjustment device 4 includes a fixed-angle plate 41 and movable-angle plate 42 matched with the fixed-angle plate 41.

In one embodiment of the present disclosure, the fixed-angle plate 41 is disposed on the first link lever 321.

Compared with the prior art, the head-mounted welding mask of the present disclosure has the following advantages:

The head-mounted welding mask provides a flip device 3 in the present disclosure, which changes the position of the barycenter of the mask shell 1 through the movement of the link mechanism 32, so that the barycenter of the mask shell 1 moves into a predetermined range that is determined based on the gravity line where the barycenter of the head-mounted mechanism 2 is located. So that reduces the pressure on welder's head after the mask shell 1 is flipped up. Since the movement trajectory of the link mechanism 32 is an arc, and the link levers of the link mechanism 32 is configured to different arm lengths, their corresponding movement trajectories are different. Therefore, on the condition that the mask shell 1 be flipped up, the height of the barycenter of the mask shell 1 can be changed according to the movement trajectory, and the barycenter can be shifted down to further improve the welder's comfort when wearing the head-mounted welding mask.

BRIEF DESCRIPTION OF THE DRAWING

By reading the detailed description of the preferred embodiments below, various other advantages and benefits will become clear to person of ordinary skill in the art. The drawings are only for the purpose of showing the preferred embodiments, and are not to limit the present invention. In which.

THE REFERENCE NUMERAL OF THE DRAWING

1—The mask shell, 11—The first hole
2—The head-mounted mechanism
21—The fixed seat, 211—The second hole, 22—The threaded pipe cap
23—The gasket
3—The flip device
31—The knob
32—The link mechanism
321—The first link lever
3211—The first-link-lever-movable-end, 3212—The first threaded tube
322—The second link lever
3221—The second-link-lever-movable-end
3222—The second-link-lever-base-end,
3223—The first protrusion
3224—The first groove, 3225—The first notch, 3226—The first limit block
323—The third link lever
3231—The third-link-lever-movable-end,
3232—The third-link-lever-base-end
3233—The second protrusion, 3234—The second notch
33—The base
331—The base-fixed-end, 332—The second limit block
333—The third limit block, 334—The second threaded tube
3341—The third protrusion
34—The press plate
4—The angle adjustment device
41—The fixed-angle plate
42—The movable-angle plate

DETAILED DESCRIPTION

The present disclosure provides many applicable creative concepts, which embodied in specific contexts. The specific examples described in the following embodiments of the present disclosure are merely exemplary illustrations of the specific embodiments of the present disclosure, and do not constitute a limitation on the scope of the present invention.

Further describe of the present disclosure below with reference to the drawings and specific embodiments.

Figure 1:
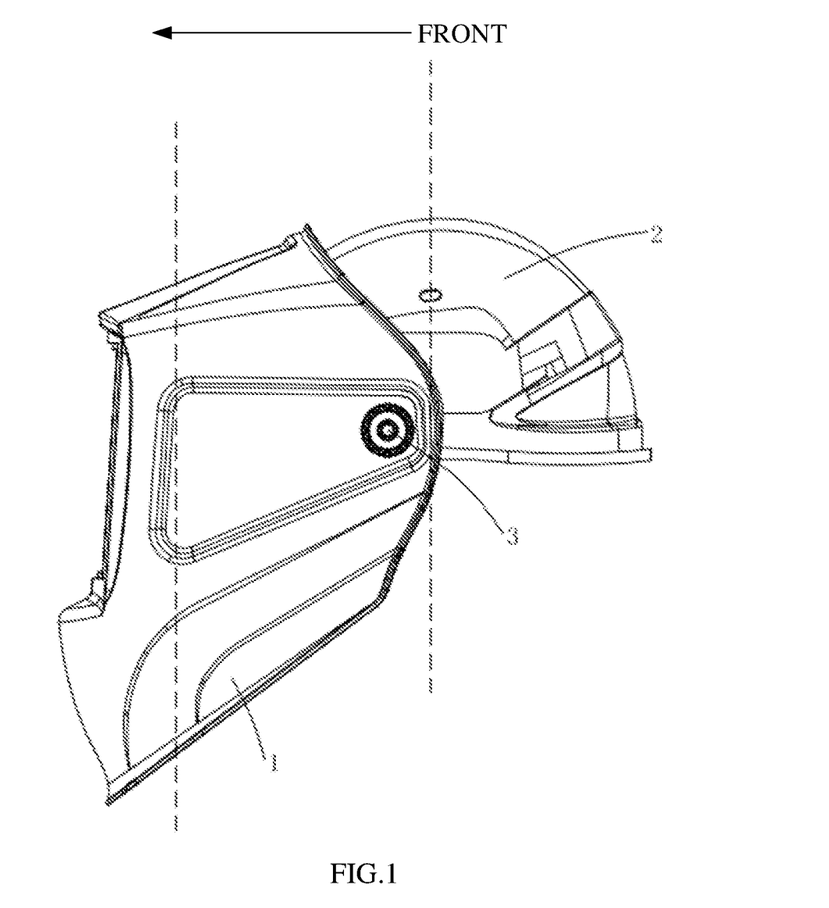
FIG. 1 is a schematic structural view of a preferred embodiment of the head-mounted welding mask before flipping up.
Figure 2:
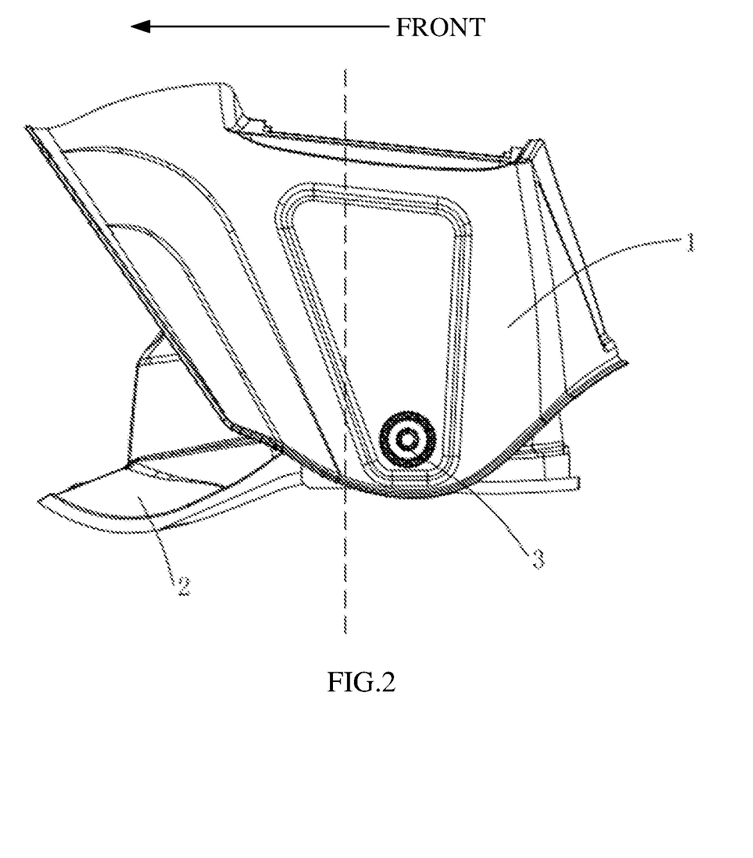
FIG. 2 is a schematic diagram of the structure of the head-mounted welding mask shown in FIG. 1 after flipping up.

As shown in FIGS. 1 and 2, FIG. 1 is a schematic structural view of a preferred embodiment of the head-mounted welding mask before flipping up. FIG. 2 is the head-mounted welding mask shown in FIG. 1 after flipping. This embodiment provides a head-mounted welding mask, which includes a mask shell 1, a head-mounted mechanism 2, and a flip device 3 configured to connect the mask shell 1 and the head-mounted mechanism 2, so that the mask shell 1 flips relative to the head-mounted mechanism 2, and the barycenter of the mask shell 1 moves into a predetermined range that is determined based on the gravity line where the barycenter of the head-mounted mechanism 2 is located. That is, before the mask shell 1 flipping up, the barycenter is located below the flip device 3, and when the mask shell 1 flipping up, for example, 90 degrees, the barycenter of the mask shell 1 moves backward into a predetermined range that is determined based on the gravity line where the barycenter of the head-mounted mechanism 2 is located.

As the main part of the head-mounted welding mask, the mask shell 1 provides the protection for the welder's head. The barycenter of the mask shell 1 is the point of the combined force of gravity of all parts of the mask shell 1.

The head-mounted mechanism 2 is configured to fix the mask shell 1 on the head of the welder when the welder wears the head-mounted welding mask. The barycenter of the head-mounted mechanism 2 is the point of the combined force of gravity of all parts of the head-mounted mechanism 2. When the welder stands upright and wears the head-mounted welding mask, the gravity line where the barycenter of the mechanism 2 is located coincides with the centerline of the welder's head. The head-mounted mechanism 2 is a headband or a safety helmet. Besides, the head-mounted mechanism 2 may also as other forms, as long as it can fix the mask shell 1 on welder's head. In an embodiment, the head-mounted mechanism 2 is a safety helmet.

Figure 3:
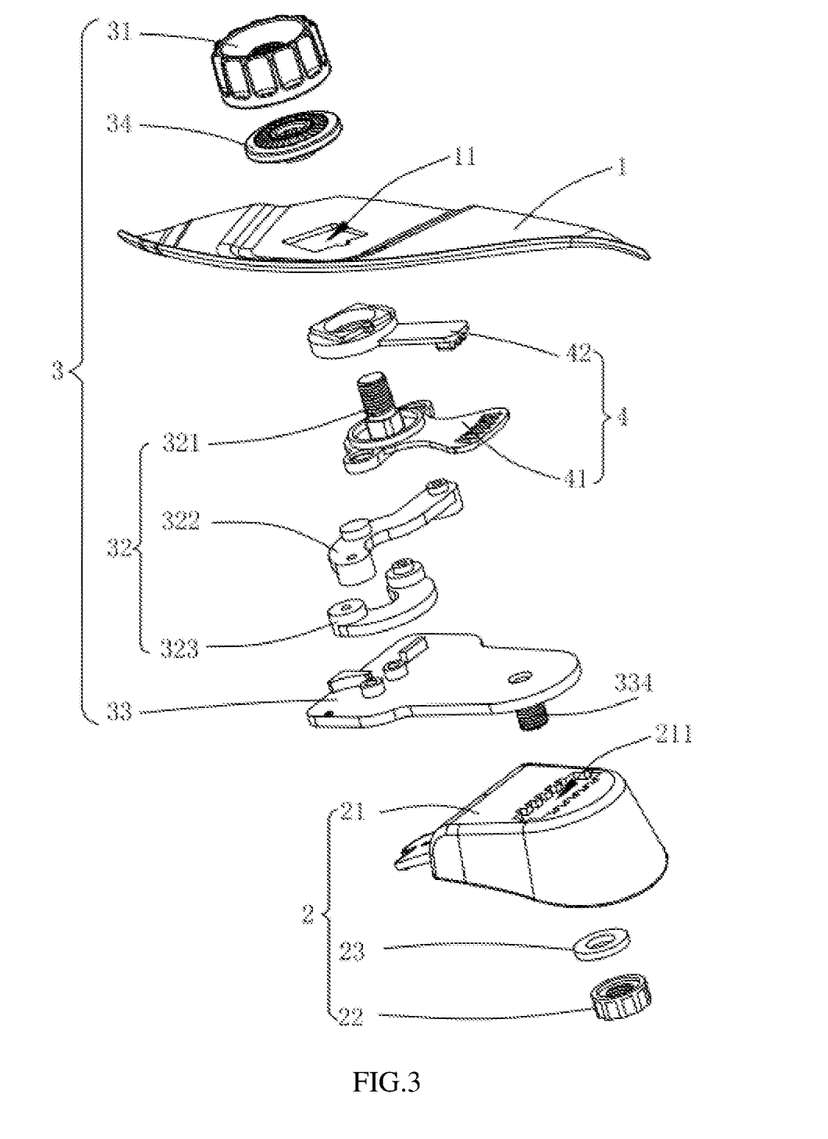
FIG. 3 is an exploded schematic view of the head-mounted welding mask shown in FIG. 1.

As shown in FIG. 3, an exploded schematic view of the head-mounted welding mask shown in FIG. 1. The flip device 3 includes a knob 31 connected to the mask shell 1, a link mechanism 32 connected to the knob 31, and a base 33 connected to the head-mounted mechanism 2. The link mechanism 32 is disposed on the base 33. When the knob 31 is moving, drives the link mechanism 32 to reciprocating in an arc, so that the mask shell 1 flips up relative to the head-mounted mechanism 2. The barycenter of the mask shell 1 moves into a range, which is preset based on the gravity line where the barycenter of the head-mounted mechanism 2 is located. Optionally, moving the mask shell 1 can also achieve the purpose.

As shown in FIGS. 1 and 2, take the welder's visual direction as the front and the reverse direction as the rear. In the present disclosure, moving the knob 31 to drive the link mechanism 32 to make an arc reciprocating movement, causes the mask shell 1 flipping backwards relative to the head-mounted mechanism 2, and the barycenter of the mask shell 1 moves backwards into the preset range.

The preset range or predetermined range is a certain distance floating in front or rear direction based on the gravity line where the barycenter of the head-mounted mechanism 2 is located. The dashed line in FIGS. 1 and 2, is the gravity line where the barycenter is located. In FIG. 1, the dashed line on the front side is the gravity line of the mask shell 1, and the dashed line on the rear side is the gravity line of the head-mounted mechanism 2. The gravity line is the weight acting line, and the line is perpendicular to the ground through the barycenter. The preset range is predetermined according to the structures of the mask shell 1 and the head-mounted mechanism 2, for example, within the scope of 1 cm in front or rear direction, but the numeric values is not limited to this but can be set according to actual demand in the present disclosure. Within the preset range, the initial position of the mask shell 1 before flipping up or the end position after flipping up meets the comfort requirements of wearing the head-mounted welding mask. That is, after flipping up, the gravity of the mask shell 1 acts uniformly on the welder's head through the head-wearing mechanism without excessive pressure on the forehead.

As shown in FIG. 2, an optimal embodiment, after flipping up, the gravity line where the barycenter of the mask shell 1 is located coincides with the gravity line where the barycenter of the head-mounted mechanism 2 is located.

In present disclosure, moving the knob 31 to drive the link mechanism 32 moving and change the position of the barycenter of the mask shell 1. After flipping up, (i.e. flipping up 90 degrees in backward direction), the barycenter of the mask shell 1 moves backward into the preset range, which is formed based on the gravity line where the barycenter of the head-mounted mechanism 2 is located. That is, the barycenter of the mask shell 1 locates nearby the centerline of the welder's head, reduces the pressure on the welder's head, improves wearing comfort. Moreover, the trajectory of the link mechanism 2 is an arc greater than 90 degrees (close to 180 degrees). When the link mechanism 32 is configured to the different lengths, the corresponding motion trajectories are different. Therefore, under the premise that the mask shell 1 can flip up, the height and the position in the front-rear direction of the mask shell's barycenter can change based on the movement trajectory. That makes the center of gravity of the mask shell nearby the centerline of the welder's head as close as possible, reduce the height of the barycenter as much as possible, move the barycenter downward, and further improve the comfort of the welder wearing the head-mounted welding mask.

The link mechanism 32 includes at least three link levers, for instance, a first link lever 321, a second link lever 322 and a third link lever 323, where the first link lever 321 is connected to the knob 31 fixedly, the second link lever 322 is rotatable connected to the first link lever 321 and the base 33 respectively, and the third link lever 323 is rotatable connected to the first link lever 321 and the base 33, respectively. When the knob 31 moves, the first link lever 321 moves synchronously also drives the second link lever 322 and the third link lever 323 rotating.

The link mechanism 32 is configured to achieve motion transformation and power transmission. The kinematic pair in the link mechanism 32 is a low pair, and the low pair is surface contacting, less pressure, more loading capacity, and better lubrication, lower wear. The link lever of the link mechanism 32 can be configured to different lengths, which can better meet the requirements of the mask shell 1 and the head-mounted mechanism 2 with different shapes and structures, with good flexibility and practical. The link lever could be plastic or metal material.

Figure 4:
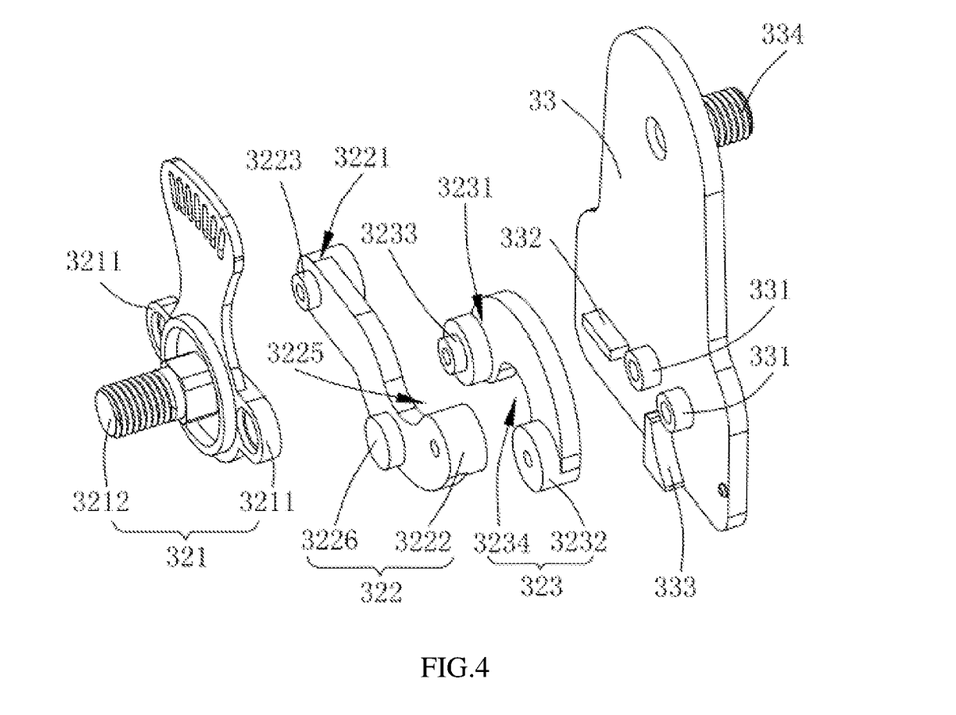
FIG. 4 is an exploded schematic view of the link mechanism and base of the head-mounted welding mask shown in FIG. 3.
Figure 5:
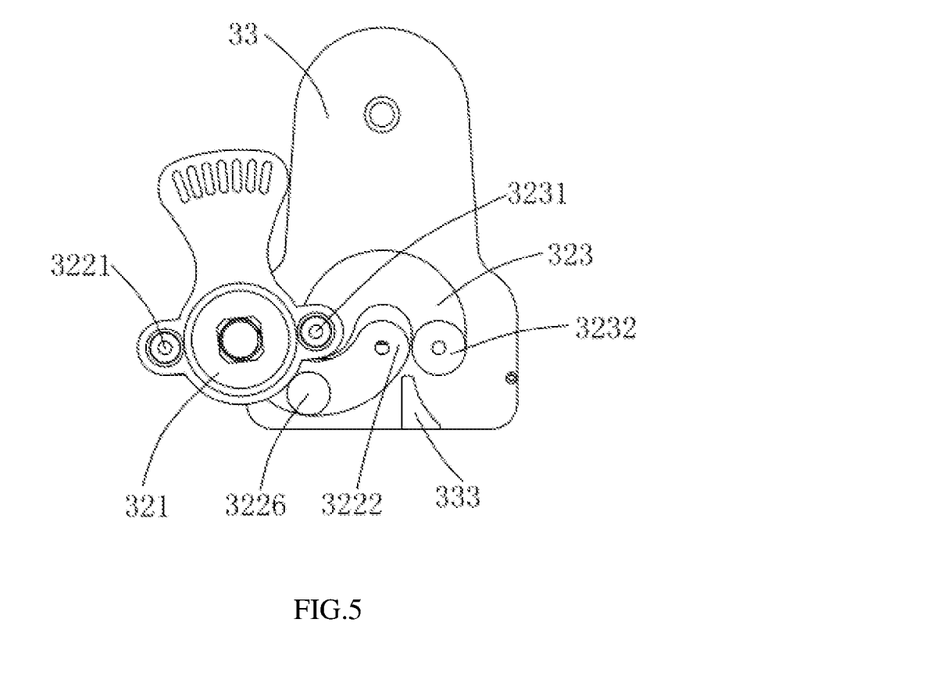
FIG. 5 is a schematic diagram of the structure of the link mechanism shown in FIG. 4 before flipping up.
Figure 6:
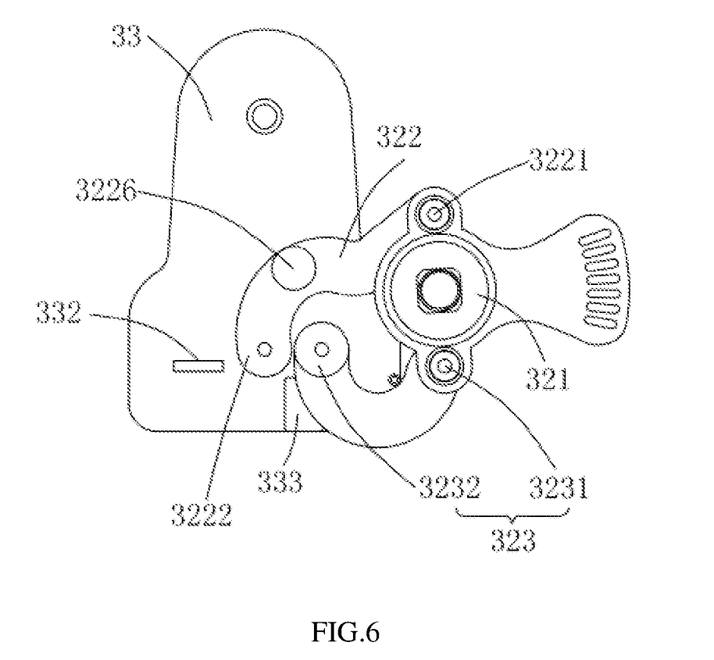
FIG. 6 is a schematic diagram of the structure in the link mechanism shown in FIG. 4 after flipping up.

As shown in FIGS. 4 to 6, FIG. 4 is a schematic exploded view of the link mechanism and base in the head-mounted welding mask shown in FIG. 3; FIG. 5 is schematic structural view of the link mechanism shown in FIG. 4 before flipping up; FIG. 6 is a schematic structural view of the link mechanism shown in FIG. 4 after flipped up. the first link lever 321 includes two first-link-lever-movable-ends 3211, and the second link lever 322 includes a second-link-lever-movable-end 3221 and a second-link-lever-base-end 3222, The third link lever 323 includes a third-link-lever-movable-end 3231 and a third-link-lever-base-end 3232, the base 33 includes two base-fixed-ends 331, and the two first-link-lever-movable-ends 3211 are respectively rotatable connected to the second-link-lever-movable-end 3221 and the third-link-lever-movable-end 3231, and the two base-fixed-ends 331 are respectively rotatable connected to the second-link-lever-base-end 3222 and the third-link-lever-base-end 3232. In the present disclosure, rotatable means that the former and the latter can be relatively rotated.

More specifically, in this embodiment, the first-link-lever-movable-end 3211 is a through hole, and the second link lever 322 provides a first protrusion 3223 on the second-link-lever-movable-end 3221. The first protrusion 3223, which runs through the corresponding the first-link-lever-movable-end 3211, is annular, so that the second-link-lever-movable-end 3221 and the first-link-lever-movable-end 3211 connected more stable and more synchronized during movement. After the first protrusion 3223 runs through the corresponding first-link-lever-movable-end 3211, a fixing member fix the two to prevent their separation in axial direction. The fixing member can be self-tapping screws, bolts or rivets. Similarly, the third link lever 323 provides a second protrusion 3233 on the third-link-lever-movable-end 3231, the second protrusion 3233, which runs through the corresponding another first-link-lever-movable-end 3211, shows the steps' morphology.

Figure 7:
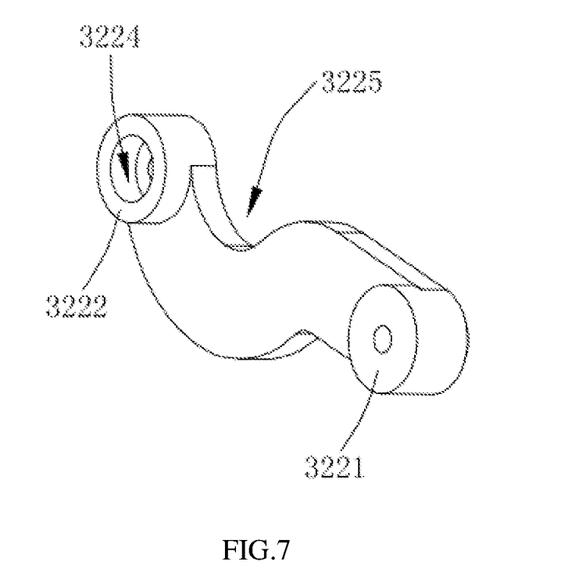
FIG. 7 is a rear view of the second link lever in the link mechanism shown in FIG. 4.

As shown in FIG. 7, a rear view of the second link lever in the link mechanism is shown in FIG. 4. The second link lever 322 provides a first groove 3224 formed from a surface of the second-link-lever-base-end 3222, and the surface is close to the base-fixed-end 331, in a direction away from the base-fixed-end 331. The first groove 3224 shows the steps' morphology, and the corresponding base-fixed-end 331 is disposed in the first groove 3224, so that the connection between the second link lever 322 and the base 33 would more tightly. Similarly, the third link lever 323 provides a second groove formed from a surface of the third-link-lever-base-end 3232 close to the base-fixed-end 331 in a direction away from the base-fixed-end 331, the corresponding another base-fixed-end 331 is disposed in the second groove.

As shown in FIG. 4, further, the second link lever 322 provides a first notch 3225. The connection structure of the third-link-lever-movable-end 3231 and the first-link-lever-movable-end 3211 disposed in the first notch 3225. So that the second link lever 322 and the third link lever 323 avoid each other without interference, and the structure is more compact. Optionally, the second link lever 322 may provide no first notch 3225, we can adjust the position of the third-link-lever-movable-end 3231 in this case. Similarly, the third link lever 323 provides a second notch 3234. The connection structure of the second-link-lever-base-end 3222 and the base-fixed-end 331 is disposed in the second notch 3234.

As shown in FIGS. 4 and 5, further, the second link lever 322 provides a first limit block 3226, which is configured to position the first link lever 321 and fix its position. Before flipping up the mask shell 1, the peripheral edge of the first limit block 3226 contact with the peripheral edge of the first link lever 321. Specifically, the first limit block 3226 is cylindrical. Optionally, the first limit block 3226 can be other shapes, including a triangle or a rectangle, etc.

Figure 8:
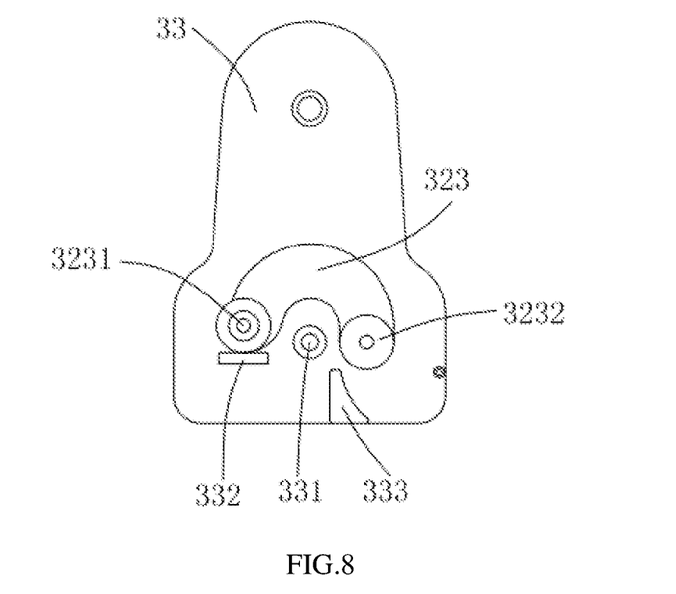
FIG. 8 is a schematic structural view of the third link lever and the base combination in the link mechanism shown in FIG. 4.

As shown in FIGS. 4 and 8, FIG. 8 is a schematic structural view of the third link lever 323 and the base 33 combination in the link mechanism 32 is shown in FIG. 4. The base 33 provides a second limit block 332, which is configured to position the third-link-lever-movable-end 3231 and fix its starting position before flipping up. Before flip up the mask shell 1, the periphery edge of the second limit block 332 contacts with the periphery edge of the third-link-lever-movable-end 3231. Correspondingly, as shown in FIGS. 4 and 7, raise up the second-link-lever-movable-end 3221 and second-link-lever-base-end 3222 of the second link lever 322, so that the shaft between is higher than the second limit block 332, to keep enough space to avoid the second limit block 332. Specifically, the second limit block 332 is rectangular. Optionally, the second limit block 332 could be other shapes, including triangle, column etc.

As shown in FIG. 6, further, a third limit block 333 is disposed on the base 33, configured to position the third-link-lever-base-end 3232, fixing its final position after flipped up. In this embodiment, as shown in FIGS. 1 and 2, the turning angle of the mask shell 1 is 90 degrees, but it may be set to other angles as necessary. After the mask shell 1 flipped up, the peripheral edge of the third limiting block is in contact with the peripheral edge of the third-link-lever-base-end 3232. Specifically, the peripheral edge of the third-link-lever-base-end 3232 is semicircular, and the peripheral edge of the third limit block 333 abutting on it is in a matching arc shape. Optionally, the third limit block 333 can be other shapes, including triangle, column, rectangle, etc.

As shown in FIG. 3, the knob 31 is configured to cooperate with the link mechanism 32, to fixed connect the flip device 3 and the mask shell 1, and lock them. Specifically, a first threaded tube 3212 disposed between the two first-link-lever-movable-end 3211 of the first link lever 321 in the link mechanism 32. A first pipe disposed on the mask shell 1 correspond, the first threaded tube 3212 penetrates the first hole 11 on the mask shell 1, the knob 31 is screwed to the first threaded tube 3212, tighten the knob 31, and then fix the flip device 3 and the mask shell 1 together. Optionally, the knob 31 also could be other structures, including screws, rivets, etc., which could fix the flip device 3 and the mask shell 1 together.

As shown in FIG. 3, further, the flip device 3 further includes a press plate 34 sandwiched between the mask shell 1 and the knob 31. The press plate 34 is in a ring shape, with a hollow inside as a mounting hole. The first threaded tube 3212 penetrates the press plate 34; the press plate 34 is installed on the first hole 11 of the mask shell 1 and cooperates with the knob 31 to press the mask shell 1, makes the mask shell 1 and the flip device 3 fixed more firmly and stably, and more integration.

As shown in FIG. 3, the base 33 is configured to cooperate with the link mechanism 32 to fix connect the flip device 3 and the head-mounted mechanism 2, play a fixed role. Specifically, a second threaded tube 334 is disposed on the base 33. A fixed seat 21 configured to mount the base 33, a threaded pipe cap 22 configured to match with the second threaded tube 334, and a gasket 23, are disposed on the head-mounted mechanism 2. The fixed seat 21 includes a second hole 211; the second threaded tube 334 penetrates the second hole 211 and the gasket 23 in sequence, and then employs a screwed joint with the threaded pipe cap 22. The connection makes the base 33 fix to the fixed seat 21, so that connect the flip device 3 and the head-mounted mechanism 2 integration.

Figure 9:
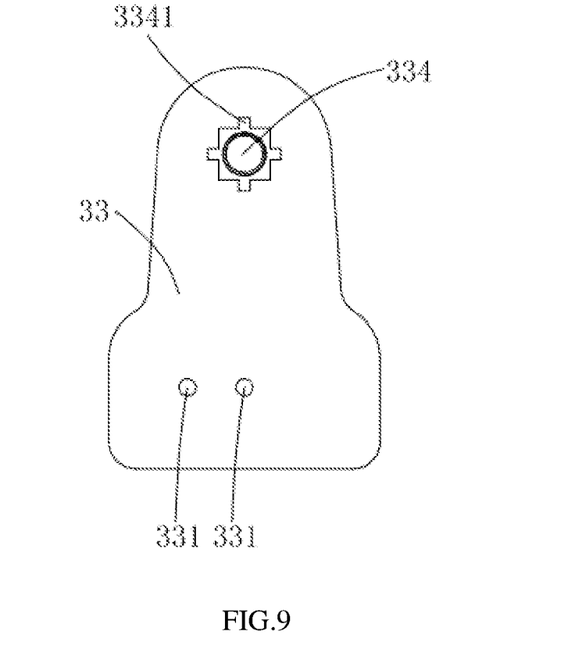
FIG. 9 is a rear view of the base in the link mechanism shown in FIG. 4.

As shown in FIG. 9, FIG. 9 is a rear view of the base in the link mechanism shown in FIG. 4. The second hole 211 provides a plurality of spaced grooves along its edge, the base 33 provides a third protrusion 3341 corresponding to the groove on the periphery of the second threaded tube 334. When the second threaded tube 334 goes through the second hole 211, the third protrusion 3341 corresponds to the shape of the groove, and the fixing effect is better.

As shown in FIG. 3, further, the head-mounted welding mask further includes an angle adjustment device 4, which configure to adjust the angle between the mask shell 1 and the welder's eyes. The angle adjustment device 4 includes a fixed-angle plate 41 and a movable-angle plate 42 that cooperates with the fixed-angle plate 41. Specifically, the fixed-angle plate 41 is disposed on the first link lever 321, for simplifying the structure and reducing the cost; the movable-angle plate 42 is disposed between the first link lever 321 and the mask shell 1. The movable-angle plate 42 provides a mounting hole. During installation, the first threaded tube 3212 penetrates the movable-angle plate 42 and then penetrates the first hole 11 and the press plate 34 in sequence, and then connects to the knob 31.

The movable-angle plate 42 is rotated relative to the fixed-angle plate 41 to drive the mask shell 1 to rotate, to adjust the angle between the mask shell 1 and the welder's eyes when the welder wears the head-mounted welding mask. The movable-angle plate 42 can be rotated and different gears and gears span can be set according to the rotation angle.

It should be noted that the number of both the flip device 3 and the angle adjustment device 4 are two, which are symmetrically provided on both sides of the mask shell 1.

It should be noted that the above-mentioned embodiments illustrate rather than limit the present invention, and those skilled in the art can design alternative embodiments without departing from the scope of the appended claims. In the claims, any reference signs between parentheses should not be constructed as limitations on the claims. The word "comprising" does not exclude the presence of elements or steps not listed in the claims.

I claim:

1. A head-mounted welding mask, which comprises a mask shell (1), a head-mounted mechanism (2), and a flip device (3) configured to connect the mask shell (1) and the head-mounted mechanism (2), wherein the flip device (3) comprises a knob (31) which is connected to the mask shell (1), a link mechanism (32) which is connected to the knob (31), and a base (33) which is connected to the head-mounted mechanism (2), the link mechanism (32) is disposed on the base (33), when the knob (31) is moved, the knob (31) drives the link mechanism (32) to reciprocate in an arc, so that the mask shell (1) flips relative to the head-mounted mechanism (2), and the barycenter of the mask shell (1) moves into a predetermined range that is determined based on the gravity line where the barycenter of the head-mounted mechanism (2) is located, and wherein the link mechanism (32) comprises at least a first link lever (321), a second link lever (322), and a third link lever (323), the first link lever (321) is connected to the knob (31) fixedly, the second link lever (322) is rotatable connected to the first link lever (321) and the base (33) respectively, and the third link lever (323) is rotatable connected to the first link lever (321) and the base (33), respectively, the first link lever (321) comprises two first-link-lever-movable-ends (3211), and the second link lever (322) comprises a second-link-lever-movable-end (3221) and a second-link-lever-base-end (3222), the third link lever (323) comprises a third-link-lever-movable-end (3231) and a third-link-lever-base-end (3232), the base (33) comprises two base-fixed-ends (331), and the two first-link-lever-movable-ends (3211) are respectively rotatable connected to the second-link-lever-movable-end (3221) and the third-link-lever-movable-end (3231), and the two base-fixed-ends (331) are respectively rotatable connected to the second-link-lever-base-end (3222) and the third-link-lever-base-end (3232).

2. The head-mounted welding mask according to claim 1, wherein the second link lever (322) provides a first notch (3225), and the third-link-lever-movable-end (3231) is disposed in the first notch (3225).

3. The head-mounted welding mask according to claim 1, wherein the second link lever (322) provides a first limit block (3226), configured to position the first link lever (321).

4. The head-mounted welding mask according to claim 1, wherein the base (33) provides a second limit block (332), configured to position the third-link-lever-movable-end (3231).

5. The head-mounted welding mask according to claim 1, wherein the base (33) provides a third limit block (333), configured to position the third-link-lever-base-end (3232).

6. The head-mounted welding mask according to claim 1, wherein the head-mounted mechanism (2) is a headband or a safety helmet.

7. The head-mounted welding mask according to claim 1, wherein the head-mounted welding mask further comprises an angle adjustment device (4), configured to adjust the angle between the mask shell (1) and the welder's eyes, the angle adjustment device (4) comprises a fixed-angle plate (41) and movable-angle plate (42) matched with the fixed-angle plate (41).

8. The head-mounted welding mask according to claim 7, wherein the fixed-angle plate (41) is disposed on the first link lever (321).

* * * * *